US010690617B2

(12) United States Patent
Hughes et al.

(10) Patent No.: US 10,690,617 B2
(45) Date of Patent: Jun. 23, 2020

(54) SYSTEMS AND METHODS FOR ELECTROCHEMICAL KETONE DETECTION AND MEASUREMENT

(71) Applicant: Polymer Technology Systems, Inc., Indianapolis, IN (US)

(72) Inventors: Gary L. Hughes, Camby, IN (US); Aniruddha Patwardhan, Fishers, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 12 days.

(21) Appl. No.: 15/134,156

(22) Filed: Apr. 20, 2016

(65) Prior Publication Data

US 2016/0327562 A1 Nov. 10, 2016

Related U.S. Application Data

(60) Provisional application No. 62/158,446, filed on May 7, 2015.

(51) Int. Cl.
*G01N 27/327* (2006.01)
*C12Q 1/00* (2006.01)

(52) U.S. Cl.
CPC ......... *G01N 27/3272* (2013.01); *C12Q 1/004* (2013.01); *C12Q 1/005* (2013.01); *C12Q 1/006* (2013.01); *G01N 2333/904* (2013.01); *G01N 2333/90209* (2013.01); *G01N 2800/042* (2013.01); *G01N 2800/085* (2013.01)

(58) Field of Classification Search
None
See application file for complete search history.

(56) References Cited

U.S. PATENT DOCUMENTS

| 7,955,484 B2* | 6/2011 | Cai | G01N 33/66 204/403.04 |
| 2004/0043376 A1* | 3/2004 | Gupta | C12Q 1/32 435/4 |
| 2004/0134779 A1* | 7/2004 | Hsu | B01L 3/508 204/403.03 |
| 2011/0094882 A1* | 4/2011 | MacFie | G01N 27/3272 204/403.03 |
| 2013/0075276 A1 | 3/2013 | Hoashi et al. | |

(Continued)

FOREIGN PATENT DOCUMENTS

| GB | 2337122 A | 11/1999 |
| WO | WO 01/46457 A2 | 6/2001 |
| WO | WO 03/065875 A2 | 8/2003 |

OTHER PUBLICATIONS

Zhang et al. (Acta Cryst. E68, o2101) (Year: 2012).*

(Continued)

*Primary Examiner* — Gurpreet Kaur
*Assistant Examiner* — Steven E Rosenwald
(74) *Attorney, Agent, or Firm* — Haynes and Boone, LLP

(57) ABSTRACT

A system for the electrochemical detection of ketone levels includes a test strip including an electrode and a counter electrode, the electrode and counter electrode located in a sample reception area. The system further includes a coating on one of the electrode and counter electrode, the coating including a mediator for ketones. Optionally, the mediator is ferricyanide.

6 Claims, 4 Drawing Sheets

(56) References Cited

U.S. PATENT DOCUMENTS

2014/0124384 A1* 5/2014 Gerber ................ A61B 5/0002
  205/782
2014/0127728 A1  5/2014 Wilsey

OTHER PUBLICATIONS

International Search Report dated Jul. 21, 2016 issued in related PCT App. No. PCT/US2016/028469 (2 pages).
International Preliminary Report on Patentability dated Nov. 7, 2017 issued in related PCT App. No. PCT/US2016/028469 (9 pages).
European Search Report dated Oct. 4, 2018 issued in related European Patent App. No. 16789747.9 (8 pages).

* cited by examiner

SYSTEMS AND METHODS FOR ELECTROCHEMICAL KETONE DETECTION AND MEASUREMENT

CROSS-REFERENCE TO RELATED APPLICATIONS

This application claims the benefit of Provisional Application No. 62/158,446 filed on May 7, 2015, titled "Systems And Methods For Electrochemical Ketone Detection And Measurement," the entire disclosure of which is hereby incorporated by reference.

BACKGROUND

Point of Care ("POC") and home testing for various blood analytes and other detectable metrics in bodily fluids is desirable for patient and doctor. In many scenarios, patients and doctors can determine critical features related to the immediate and long-term health of patients with a simple test strip used with meters or other point-of-care analysis devices. These devices are usually simple to use and provide results within minutes. B-hydroxybutyrate, a ketone, is one such detectable analyte. Ketones are the end products of fatty acid metabolism (ketosis). The presence and severity of ketosis can be determined by measuring blood levels for B-hydroxybutyrate. Ketosis can be dangerous when ketones build up in the body. The testing of ketones may be important in those individuals with diabetes, since it may be an indicator of additional insulin and sugar production, usage, and storage issues.

BRIEF SUMMARY

In one embodiment, a system for the electrochemical detection of ketone levels includes a test strip including an electrode and a counter electrode, the electrode and counter electrode located in a sample reception area. The system further includes a coating on one of the electrode and counter electrode, the coating including a mediator for ketones. Optionally, the mediator is ferricyanide. In one configuration, the coating additionally includes hydroxybutyrate dehydrogenase and nicotinamide adenine dinucleotide (NAD). Alternatively, the coating additionally includes diaphorase. In one alternative, the coating includes 1-Methoxy-5-methylphenazinium methylsulfate. Optionally, the coating includes a buffer and a surfactant.

In another embodiment, a system for the electrochemical detection of ketone and glucose levels includes a test strip including a first electrode and a first counter electrode and a second electrode and a second counter electrode, the first electrode and first counter electrode located in a first sample reception area and the second electrode and second counter electrode located in a second sample reception area. The system further includes a first coating on one of the first electrode and first counter electrode, the first coating including a mediator for ketones. In one alternative, the system further includes a second coating on one of the second electrode and second counter electrode, the second coating including a mediator for glucose. Optionally, the mediator for ketones is ferricyanide. Alternatively, the first coating additionally includes hydroxybutyrate dehydrogenase and NAD. In one alternative, the first coating additionally includes diaphorase. In another alternative, the first coating includes 1-Methoxy-5-methylphenazinium methylsulfate. Optionally, the first coating includes a buffer and a surfactant. In one configuration, the second coating includes 1-Methoxy-5-methylphenazinium methylsulfate. Optionally, the second coating does not include diaphorase.

In one embodiment, a method of detecting ketones includes providing an electrochemical test strip and placing the electrochemical test strip in a meter. The method further includes placing a blood sample on the electrochemical test strip and measuring a current provided through the blood sample and the electrochemical test strip. The method further includes calculating a level of ketones with the meter based on the current. Optionally, the test strip includes an electrode and a counter electrode, the electrode and counter electrode located in a sample reception area; and a coating on one of the electrode and counter electrode, the coating including a mediator for ketones. In one alternative, the mediator is ferricyanide. Optionally, the coating additionally includes hydroxybutyrate dehydrogenase, NAD, and diaphorase. Alternatively, the coating includes a buffer and a surfactant. In one embodiment, the method further includes measuring a second current provided through the blood sample and the electrochemical test strip and calculating a level of glucose with the meter based on the second current.

DETAILED DESCRIPTION

Figure 1A:
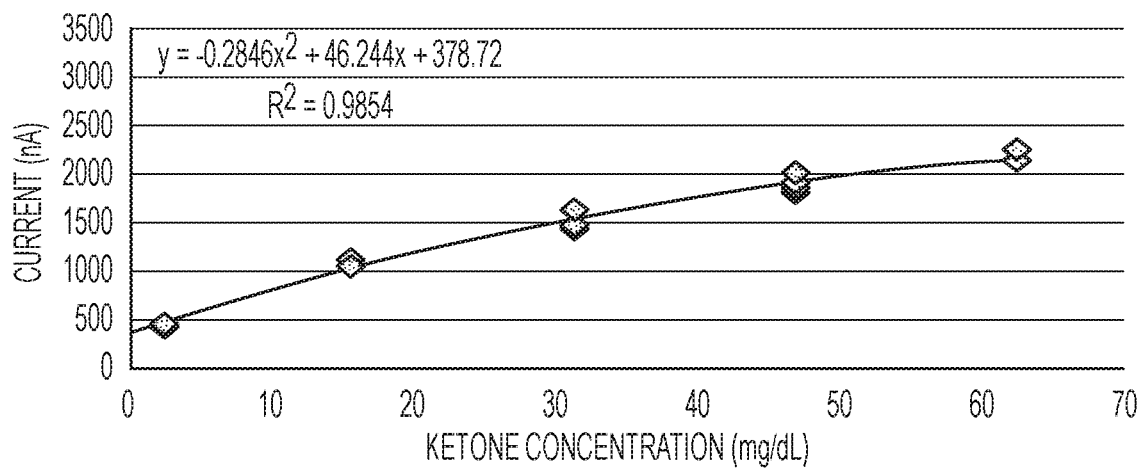
FIGS. 1a-1d show the results of the testing of one embodiment of a test strip for ketone detection with an electrical source adapted to provide different startup times.
Figure 1B:
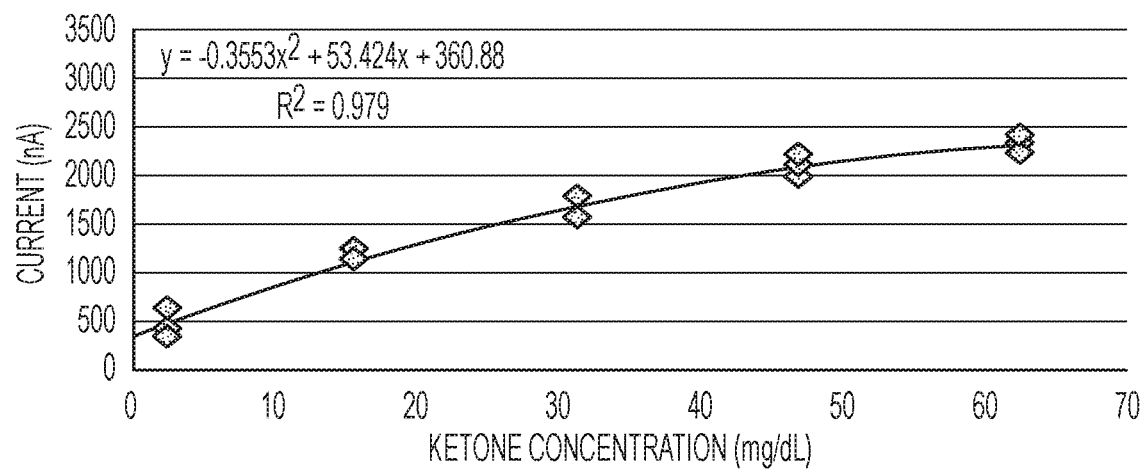
Figure 1C:
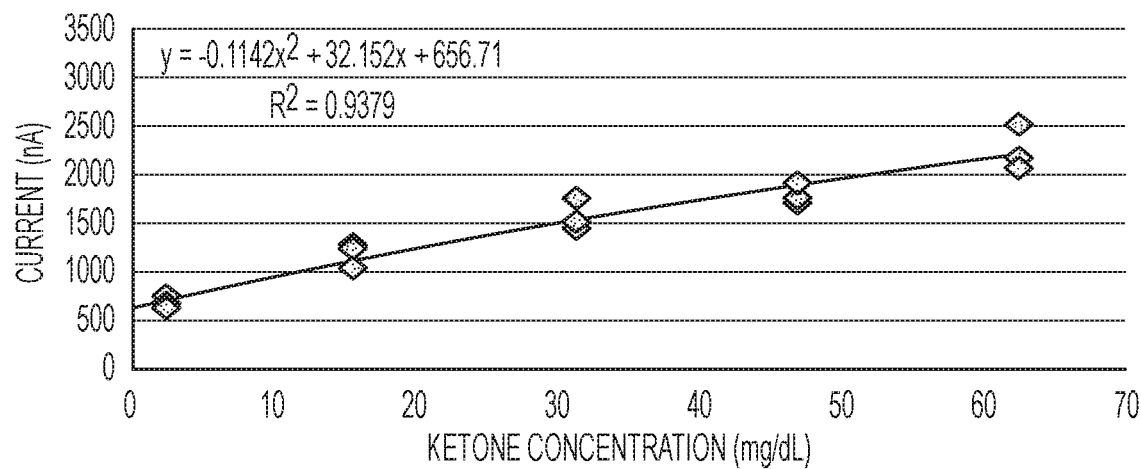
Figure 1D:
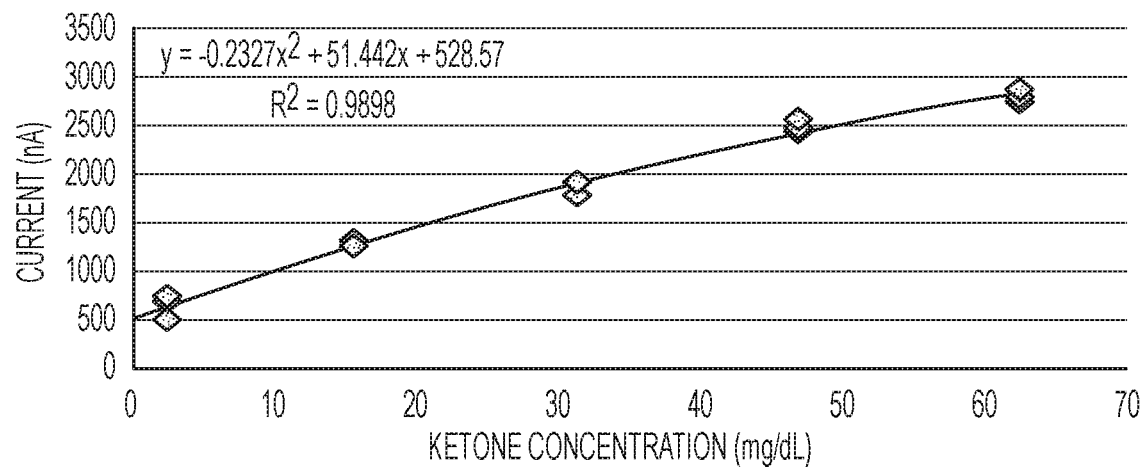

Certain terminology is used herein for convenience only and is not to be taken as a limitation on the embodiments of the systems and methods for electrochemical ketone determination. In the drawings, the same reference letters are employed for designating the same elements throughout the several figures. As stated above, ketone may be an indicator for liver health and function. Periodic tests for ketone levels may allow patients to address liver concerns before they become a significant issue.

Traditionally, point-of-care tests for ketones have been reflectance based. Due to the reactants in the reaction membrane, the membrane may be prone to yellowing. This yellowing may modify the optical signal measured. The yellowing may cause an increased signal (over-recovery) at low analyte concentration and decreased signal (under-recovery) at high analyte concentration. The yellowing is due at least in part to a somewhat unstable chromophore. To avoid working with an unstable chromophore, it is possible to conduct the ketone assay as an electrochemical test. By exchanging the chromophore for a mediator for electrochemical assays, the assay would be much more stable.

The creation of an electrochemical ketone test strip assay provides for:

1. Increased stability of the ketone test strip.
2. Less blood applied to the strip. By going to an amperometric test, the blood volume can be decreased from 15 µL to approximately 1.2 µL or less.
3. Faster reaction time. Since electrochemical tests are generally not endpoint tests, the reaction time can be faster.
4. Precision is typically better with an amperometric test.

5. The ability to have a diabetic panel—glucose and ketone in a single electrochemical test strip. This kind of test strip does not exist on the market.

Additional advantages of the electrochemical ketone strip include:

1. The strip should have a longer expiration date and not be plagued by chromophores that are sensitive to light or oxygen.
2. Less blood applied to strip. By going to an amperometric test, we can decrease the blood volume from 15 µL to approximately 1.2 µL or less.
3. Faster reaction time. Since electrochemical tests generally are not endpoint tests, the reaction time can be faster.
4. Precision typically is better with an amperometric test.
5. The ability to have a diabetic panel—glucose and ketone in a single electrochemical test strip.

Embodiments of a ketone reflectance strip assay uses a tetrazolium dye that is not stable and photosensitive. This creates a yellowing of the reaction membrane causing over-recovery at low analyte concentrations and under-recovery at high analyte concentrations. Due to this chromophore issue, it is desired to measure β-hydroxybutyrate (ketone) levels in a better way. Due to the reaction scheme, the problematic chromophore may be removed, replaced with a mediator to create an electrochemical ketone test. This concept has been shown to work in mockups for electrochemical testing. It may be possible to additionally optimize the reagents. The move to this technology will provide a more stable test strip with longer shelf life with all the added benefits of amperometric testing—smaller sample volumes, faster reaction times, and better precision.

In addition to glucose testing, sometimes diabetics need to check β-hydroxybutyrate (ketone) levels. The American Diabetes Association recommends that ketone testing should be performed during illness and whenever glucose levels are consistently high. (See American Diabetes Association, Tests of Glycemia in Diabetes, Diabetes Care, 2004; 27 (51):591-93.) Furthermore, it is recommended that ketone testing be done in blood since the presence of β-hydroxybutyrate in blood indicates the onset of ketosis earlier than the detection of acetoacetate in urine. It may be preferable to have a single test strip that tests both ketone and glucose for the diabetic population or have a meter that can conduct both tests. A diabetic panel of electrochemical glucose and ketones is not commercially available from any diagnostic company. However, because of this invention, the door is opened to allow for the first commercial development of an amperometric diabetic/glucose panel—glucose and ketones.

The following reaction is the proposed reaction for creating an electrochemical ketone test. The reflectance-based test currently marketed uses tetrazolium salt Nitro-TB in place of the mediator ferricyanide resulting in a formazan dye. Instead of a color change, the reaction is now measuring current (nA) produced. The reaction pathway is shown below.

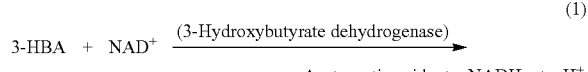
(1)

(2)

In one method of manufacture of electrochemical strips for ketone detection, blank carbon electrode strips were coated with ketone reagent containing buffer, surfactant, hydroxybutyrate dehydrogenase, NAD, ferricyanide, and diaphorase in the same ratios and concentration as the reflectance assay. The reagent was dried on the strips in a convection oven.

The ketone strips were tested on a potentiostat having the capabilities of manipulating the incubation time, potential applied, etc. The potential was set at 300 mV and varying incubation periods tested. Initially, only serum samples were tested. Additional optimzation may be available for the electrochemical assay, but initial testing has demonstrated that an assay is possible. The results are seen in FIGS. 1a-1d. As is clear from the figures, the R squared is good and, additionally, the intercept is at a reasonable level. A delay in measurement appears to deliver a more linear trend-line.

Figure 2:
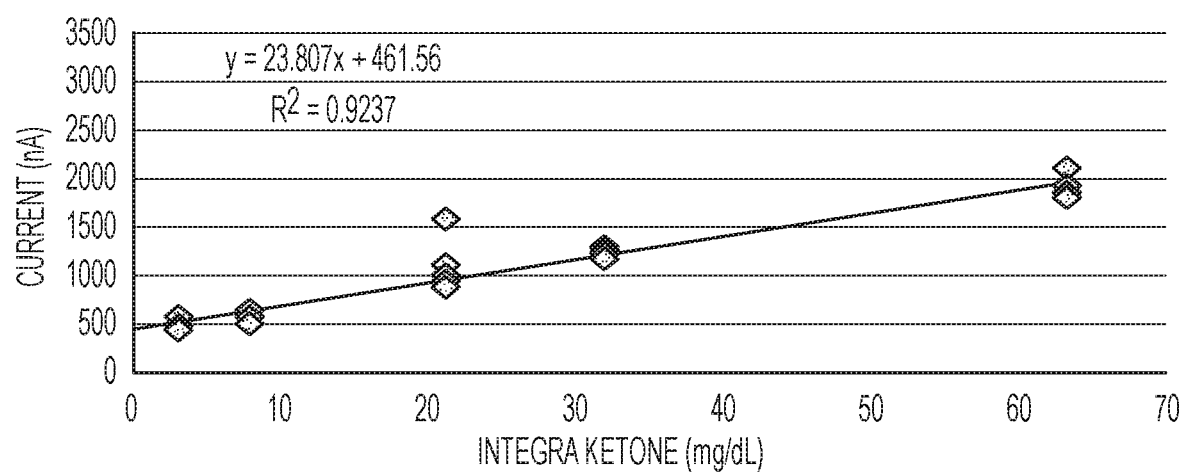
FIG. 2 shows the results of the testing of the test strip for ketone detection of FIGS. 1a-1d tested on a portable meter.

In another round of testing, it was the CardioChek Plus® version 1.05 meter was used to determine the performance of an electrochemical ketone test being constrained by no incubation period, 400 mV potential, and a maximum of 20 seconds testing time. Compared to the potentiostat, the parameters in the CardioChek Plus® are fairly fixed. The assay may be optimized further for reagents, potential applied, and testing time. FIG. 2 below demonstrates the results using whole blood and the CardioChek Plus® meter. The intercept and the R squared value show reasonable potential considering that further optimization may be available.

Figure 3:
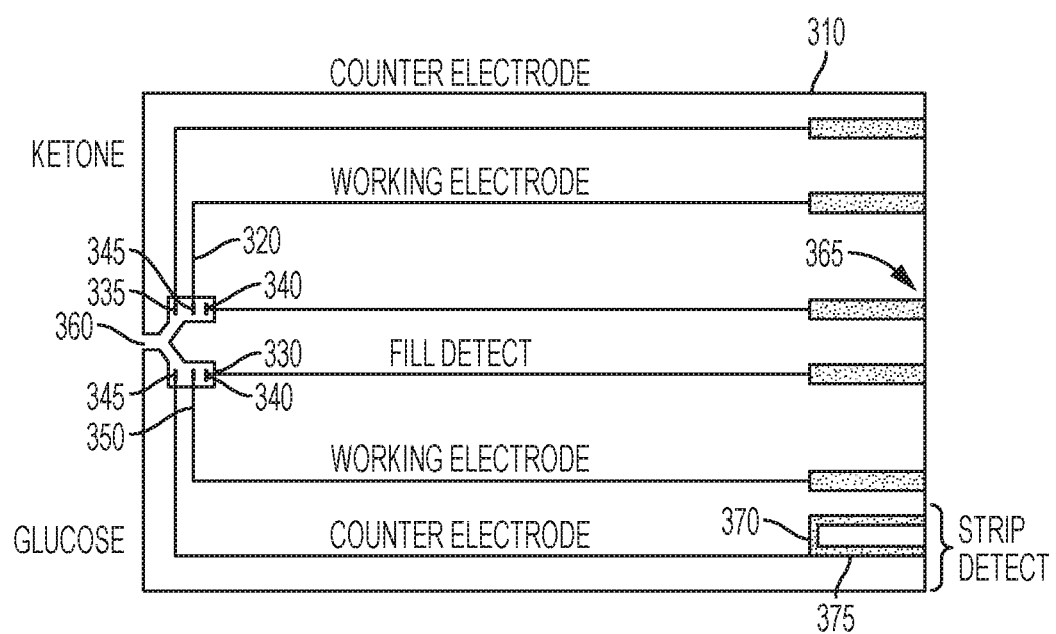
FIG. 3 shows one embodiment of a dual analyte electrochemical test strip for glucose and ketones.

One of the added advantages of embodiments of an electrochemical ketone test strip is the ability to make an amperometric diabetic panel for testing both glucose and ketone. FIG. 3 shows one embodiment of a drawing depicting how such a strip might appear. Each test will operate independently but will only require one small drop of blood.

In FIG. 3, test strip 310 includes a ketone section 320 and a glucose section 330. In the ketone section 320, a working electrode 335 and a counter electrode 345 may be provided. Additionally, two fill detect electrodes 340 may be provided. Current through these fill detect electrodes 340 from working electrodes 335, 345 ensure that blood has filled the chamber indicating that the sample size is sufficient. In the glucose section 320, an additional working electrode 345 and a counter electrode 350 may be provided. In operation, a blood sample may be applied to the sample inlet 360 of the strip. The contact area 365 of the test strip may be provided for each electrode and fill detector. Additionally, a strip detection electrode 370 may be provided for one of the working contacts 375, such that a circuit independent of the analysis circuits may be established to indicate insertion of the test strip in the meter.

Calibration curves and testing protocols may be included as part of a meter and test strip system. In addition to using a meter, various electronic devices may be configured to receive the test strip and perform testing. Calculation of ketone and glucose levels may be done remotely or at the electronic device providing the current to the test strip.

In conclusion, we have shown the ability to produce an electrochemical ketone test strip. This assay should display better precision and have a longer shelf life with smaller sample volumes and faster reaction times. Having an electrochemical test also opens possibilities of creating a novel diabetic panel to test both glucose and ketones.

In some alternatives of use for a glucose detection system, diaphorase is not used and 1-Methoxy PMS is used instead.

In many embodiments, parts of the system are provided in devices including microprocessors. Various embodiments of systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each attachment may be interchanged between embodiments.

What is claimed as new and desired to be protected by Letters Patent of the United States is:

1. A system for the electrochemical detection of ketone and glucose levels, the system comprising:
    a test strip including a first electrode and a first counter electrode and a second electrode and a second counter electrode, the first electrode and first counter electrode located in a first sample reception area and the second electrode and second counter electrode located in a second sample reception area, the first and second sample reception areas interconnected via an inlet, each of the first and second sample reception areas being separate; and
    a first coating on one of the first electrode and first counter electrode, the first coating including a mediator for ketones, wherein the first coating additionally includes diaphorase and the first coating includes 1-Methoxy-5-methylphenazinium methylsulfate;
    a second coating on one of the second electrode and second counter electrode, the second coating including a mediator for glucose; wherein the mediator for ketones is ferricyanide, the first coating additionally includes hydroxybutyrate dehydrogenase, and nicotinamide adenine dinucleotide (NAD) and wherein the second coating includes 1-Methoxy-5-methylphenazinium methylsulfate and the second coating does not include diaphorase; and
    a meter engaging the test strip having an electrical source configured to provide different startup times for the first electrode and first counter electrode and the second electrode and second counter electrode.

2. The system of claim 1, wherein the first coating includes a buffer and a surfactant.

3. The system of claim 1, wherein the first and second sample reception areas form respective first and second sample chambers separated from each other.

4. The system of claim 3, wherein the first and second sample chambers are separated by a dividing wall.

5. A system for the electrochemical detection of ketone and glucose levels, the system comprising:
    a test strip including a first electrode and a first counter electrode and a second electrode and a second counter electrode, the first electrode and first counter electrode located in a first sample chamber, the second electrode and second counter electrode located in a second sample chamber, the first and second sample chambers divided by a dividing wall and interconnected via an inlet;
    a first coating on one of the first electrode and first counter electrode, the first coating including a mediator for ketones and including hydroxybutyrate dehydrogenase, 1-Methoxy-5-methylphenazinium methylsulfate and nicotinamide adenine dinucleotide (NAD), wherein the mediator for ketones is ferricyanide; and
    a second coating on one of the second electrode and second counter electrode, the second coating including a mediator for glucose, and wherein the second coating includes 1-Methoxy-5-methylphenazinium methylsulfate and the second coating does not include diaphorase.

6. The system of claim 5, further comprising a meter engaging the test strip, the meter having an electrical source configured to provide different startup times for the first electrode and first counter electrode and the second electrode and second counter electrode.

* * * * *